United States Patent [19]

Wiegand et al.

[11] Patent Number: 5,783,455
[45] Date of Patent: Jul. 21, 1998

[54] REGENERABLE SOLID PHASE FOR CARRYING OUT SPECIFIC BINDING REACTIONS

[75] Inventors: Andreas Wiegand, Schwalmstadt; Rudolf Schmidtberger, Marburg, both of Germany

[73] Assignee: Behring Diagnostics GmbH, Marburg, Germany

[21] Appl. No.: 542,026

[22] Filed: Oct. 12, 1995

[30] Foreign Application Priority Data

Oct. 15, 1994 [DE] Germany ............... 44 36 910.7

[51] Int. Cl.[6] ................................................ G01N 33/553
[52] U.S. Cl. ..................... 436/525; 435/7.1; 435/970; 436/518; 436/810
[58] Field of Search ............... 427/2.11; 435/7.1, 435/970, 969; 436/518, 525, 528–531, 810

[56] References Cited

U.S. PATENT DOCUMENTS

| | | | |
|---|---|---|---|
| 4,054,646 | 10/1977 | Giaever. | |
| 4,279,998 | 7/1981 | Shahani et al. | 435/174 |
| 4,971,904 | 11/1990 | Luddy | 436/518 X |
| 5,149,626 | 9/1992 | Fleming | 435/7.9 |
| 5,208,154 | 5/1993 | Weaver et al. | 435/176 |
| 5,217,594 | 6/1993 | Henkens et al. | 204/403 |

FOREIGN PATENT DOCUMENTS

| | | |
|---|---|---|
| 1047918 | 2/1979 | Canada. |
| 0 524 663 A1 | 1/1993 | European Pat. Off.. |
| 24 33 246A1 | 2/1975 | Germany. |
| WO 92/02818 | 2/1992 | WIPO. |

OTHER PUBLICATIONS

Huet et al., "Automatic Apparatus for Heterogeneous Enzyme Immunoassays . . . and Electrochemical Regeneration of the Solid Phase," Analytic Chimica Acta, vol. 272, pp. 205–212, Feb. 12, 1993.

Baymann et al, "An Electrochemical Assay for the Characterization of Redox Proteins from Biological Electron Transfer Chains," Anal. Biochem, 199:269–274 (1991).

Duschl et al, "Biologically Address Monolayer Structures Formed by Templated of Sulfur–Bearing Molecules," Biophys. J. 67: 1229–1237 (1994).

1991–1992 Millipore Catalog p. 27 "Silver Membrane Filter".

Phelps et al, "Technology for Regenerable Biosensor Probes Based on Enzyme–Cellulose Binding Domain Conjugates," Biotech. Prog. 10: 430–440 (1994).

*Primary Examiner*—Carol A. Spiegel
*Attorney, Agent, or Firm*—Finnegan, Henderson, Farabow, Garrett & Dunner, L.L.P.

[57] ABSTRACT

The present invention relates to a method for carrying out immunochemical reactions and to regenerable solid phases which can be used for this purpose. When use is made of precious metals, preferably gold, as the solid phase, and also of certain reducing agents or oxidizing agents, such as, for example, sodium borohydride and tetrabutylammonium hydroxide, with or without the addition of detergents, the solid phase can be employed repeatedly, following regeneration.

11 Claims, 1 Drawing Sheet

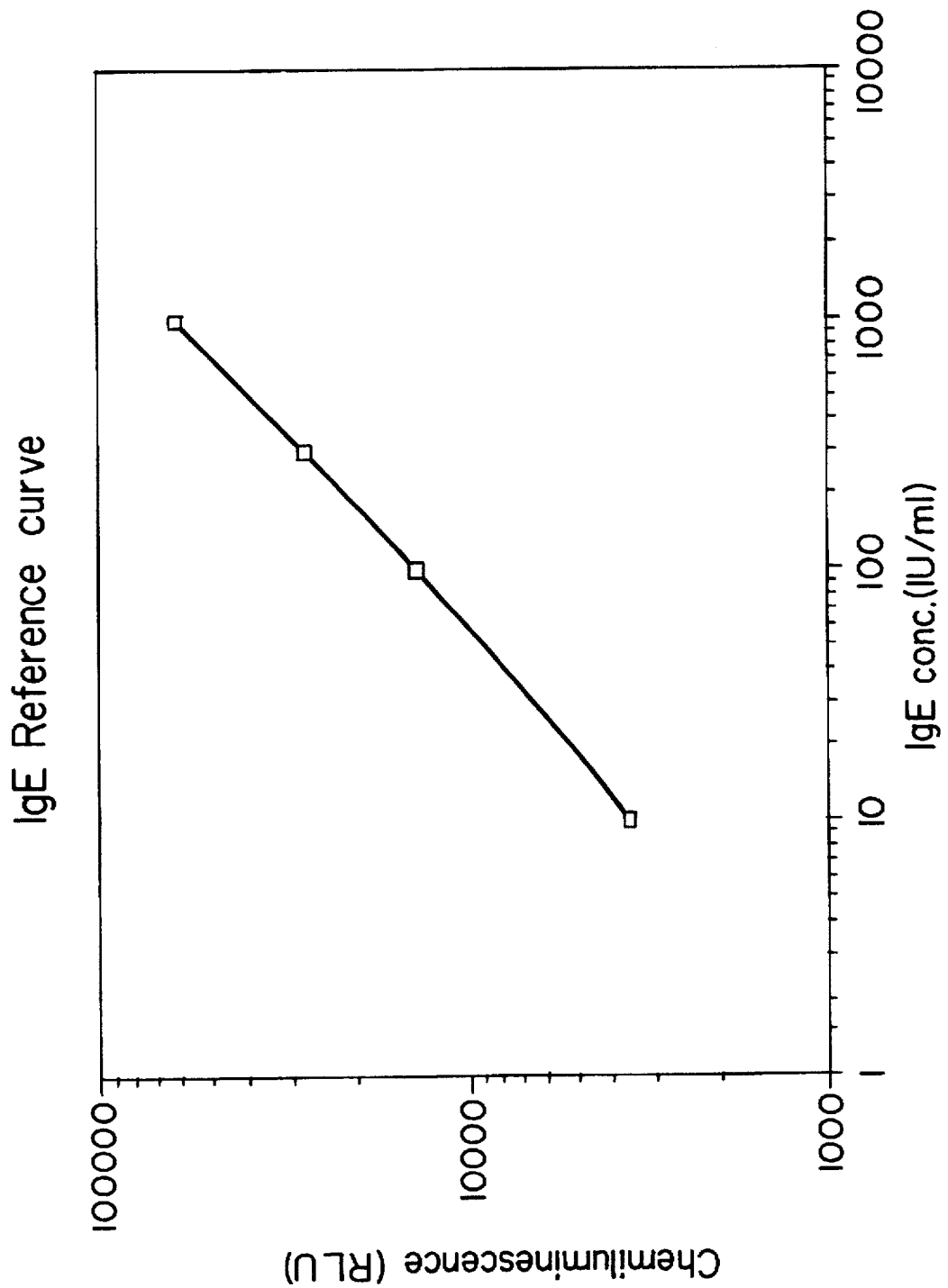

REGENERABLE SOLID PHASE FOR CARRYING OUT SPECIFIC BINDING REACTIONS

BACKGROUND OF THE INVENTION

The present invention relates to a method for carrying out immunochemical reactions and to regenerable solid phases which can be specifically used for this purpose.

Immunochemical detection methods have become very important in in vitro diagnostics. The reason for this is that they are highly specific and extremely sensitive. In addition, these methods are easy to implement.

The detection methods are based on the immunological interaction between the analyte which is to be detected and its binding partner or binding partners.

Immunological reactions are generally divided into two classes: into homogeneous methods and into heterogeneous methods. These two types of methods differ from each other in that, in the heterogeneous methods, one reaction partner is provided in excess and this excess has to be separated off from the product of the reaction. In the methods known as homogeneous assays, such a separation is not necessary since the signals of the free and bound label differ from each other.

Immunochemical methods, and their different embodiments, are known in principle to the person skilled in the art.

In order to carry out a method which is commonly employed in protein diagnostics, i.e. bound/free separation, one reaction partner is bound adsorptively or covalently to a solid phase. This technique, which is known as enzyme-linked immunosorbent assay (ELISA), is used in different variants to detect antigens or antibodies.

Since this detection technique became known, many experiments have been conducted with a view to regenerating the solid phase, together with the specific binding partner bound to it, at the end of the reaction, for example by dissociating the antigen/antibody complexes which are formed during the reaction.

However, the agents which are suitable for eliciting a dissociation of this nature, such as dilute hydrochloric acid or sulphuric acid, organic acids such as acetic acid or propionic acid, concentrated solutions of urea and solutions of chaotropic agents such as KI or KSCN, are also known to be denaturing. A further disadvantage is that these reagents rarely dissociate an antigen/antibody complex completely and this dissociation is achieved after a period of time which is unacceptably long as far as reusing is concerned.

Despite significant advances, the previously known methods for regenerating the specific binding partner which is bound to solid phases have suffered from the disadvantage that the binding properties of the solid phase have been altered to an unknown extent in each regeneration step and, as a result, these methods have thus far not been used commercially.

SUMMARY OF THE INVENTION

The present invention was therefore based on the technical problem of making available a method by which a solid phase can be reproducibly employed repeatedly for immobilizing specific binding partners in an immunological detection method.

This technical problem is solved by the provision of the embodiments which are characterized in the patent claims.

It has been observed, surprisingly, that when use is made of precious metals, preferably gold, as the solid phase, and also of certain reducing agents or oxidizing agents, such as, for example, sodium borohydride and tetrabutylammonium hydroxide, with or without the addition of detergents, the solid phase can be employed repeatedly, following regeneration.

BRIEF DESCRIPTION OF THE DRAWING

The FIGURE illustrates the ratio of IgE concentration to chemiluminescence.

DESCRIPTION OF THE PREFERRED EMBODIMENTS

In the novel method, a first specific binding partner is immobilized on a precious metal surface. After the coated surface has been washed, the analyte is caused to interact with the immobilized specific binding partner, after which washing again takes place, if appropriate. In a following step, the immobilized analyte is caused to react with a labelled, second specific binding partner. It is now possible, where appropriate after a further washing step, to measure, either directly or by means of an additional reaction, a physical or chemical quantity which is equivalent to the analyte. In the following regeneration step, one of the above described reagents is used to free the precious metal surface from the adhering molecules, and this surface is then available to be coated once again with a first specific binding partner.

The invention is particularly suitable for being incorporated into equipment, which is known per se to the person skilled in the art, which is to be employed in diagnostics. Those embodiments of the subject-matter of the invention are also advantageous in which a precious metal layer which allows the measurement signal to pass is affixed to a backing layer which likewise allows the measurement signal to pass, with it being possible for the attenuation of the signal, even when the backing layer and precious metal layer are combined, to amount to up to 90%, preferably up to 50% and very preferably up to 20%.

The essential advantage of the novel method is that the solid phase can be used as often as desired rather than, as in the prior art, a new solid phase being required for each experiment. Far fewer waste products are formed in the novel method as compared with the present state of the art. The novel method allows the user to proceed in accordance with the so-called random access principle, i.e. it is possible to carry out experiments one after the other using different first specific binding partners without being obliged to change the solid phase.

The following examples illustrate the invention.

EXAMPLE 1

Quantitative determination of human IgE by the sandwich principle using chemiluminescence-labelled antibodies Implementation of the test, and regeneration, were effected at a temperature of +37° C.

Support:

Tube made of refined gold, purity 99.99%, from DEGUSSA. External diameter: 1.5 mm Internal diameter: 0.7 mm Length 200 mm Coating:

77 µl of a solution of a (mouse) anti-human IgE monoclonal antibody (Mab) were sucked into the tube. The concentration of the Mab was 50 µl/ml. The solution also contained 75 mM Na phosphate, 75 mM NaCl and 100 g/l $Na_2SO_4$. The pH was 6.0. The Mab solution was left in the tube for 5 minutes.

Washing step:

The tube was then rinsed with 1 ml of washing buffer, i.e. a solution composed of 50 mM tris(hydroxymethyl) aminomethane (TRIS) and 50 mM citric acid, pH 7.4. The rinsing lasted for 1 minute.

Sample incubation:

77 µl of a human serum containing defined quantities of IgE were sucked into the tube and left in it for 10 minutes.

Washing step:

The tube was then rinsed for 1 minute with 1 ml of washing buffer (5 mM Na phosphate, 85 mM NaCl, 1 g/l TWEEN 20®, 0.5 g/l phenol, pH 6.5).

Conjugate reaction:

77 µl of a solution of a conjugate (prepared in analogy with example 8 from EP-A 0330 050) of (rabbit) anti-human IgE polyclonal antibodies with acridinium ester were sucked into the tube and left in it for 5 minutes. The concentration of the conjugate was 190 ng/ml, with the solution also containing 0.1M Na phosphate, 0.15M NaCl, 1 g/l h-serum albumin and 1.5 g/l TEGO BETAINE L7®, and being of pH 6.0.

Washing step:

The tube was then rinsed for 1 minute with 1 ml of a solution of 75 mM Na phosphate and 75 mM NaCl, pH 7.2.

Splitting off the bound tracer:

The tracer (acridinium ester) is split off using 77 µl of a solution composed of 0.1M $HNO_3$ and 5 g/l $H_2O_2$ and incubating for 1 minute.

Measurement:

The tube contents, containing the split-off tracer, were transferred into the measuring cuvette of an AUTOCLINI-LUMAT lumininometer, from BERTHOLD, and the luminescence reaction was triggered by adding 300 µl of 0.25M NaOH.

Regeneration of the solid phase:

The regeneration is achieved by allowing 77 µl of a solution which contains 10 g/l $NaBH_4$, and is preferably buffered (e.g. N-Cyclohexyltaurine) at between pH 7.0 and 10.0, to react for 1 minute and then rinsing for 1 minute with 1 ml of a solution containing 75 mM Na phosphate and 75 mM NaCl and being of pH 7.2.

Four samples which were tested using the above-described method and which contained differing contents of IgE produced the signal height to IgE content ratio which is depicted in the FIGURE. The latter ratio is given in international units.

EXAMPLE 2

Quantitative determination of POD

Test implementation and regeneration were carried out at a temperature of +37° C.

Support:

Tube made of refined gold, purity 99.99%, from DEGUSSA, External diameter: 1.5 mm Internal diameter: 0.7 mm Length 200 mm Coating:

77 µl of a solution of a (mouse) anti-POD monoclonal antibody in PBS (pH 7.2) were sucked into the tube. After an incubation period of 10 minutes, the capillary was rinsed with 2 ml of a 50 mmolar TRIS-citrate buffer solution (pH 7.4).

Immune reaction:

77 µl of a solution of peroxidase in IgE incubation medium (Behringwerke AG, Marburg, product no. OSND—50 mmolar phosphate, 150 mmolar NaCl, 5 mmolar TITRI-PLEX III, 0.1% RSA, 0.01% R-IgG, 10% glycerol, 2% TWEEN 20, 2 mmolar phenol, pH 6.8) were sucked into the gold capillary. After an incubation period of 10 minutes, the capillary was rinsed with 2 ml of POD washing solution, Behringwerke AG, Marburg, product no. OSEW (5 mmolar phosphate, 85 mmolar NaCl, 0.1% TWEEN 20, 0.005% phenol, pH 6.5).

Substrate reaction:

77 µl of POD chromogen, Behring, Marburg, product no. OWEY, dissolved in POD buffer, Behring, Marburg, product no. OWEZ, were sucked into the tube. After an incubation period of 5 minutes, 50 µl of the solution contained in the capillary were removed.

Stopping:

50 µl of POD stop solution (Behringwerke AG, Marburg, product no. OSFA) were added to the 50 µl removed from the capillary.

Detection:

Measurement of the extinction of the resulting solution in a photometer at 492 nm.

Regeneration of the solid phase:

The gold capillary was rinsed with 5 ml of a 20% by weight solution of tetrabutylammonium hydroxide. The capillary was then rinsed with 1 ml of a phosphate-buffered solution of sodium chloride (pH 7.2).

We claim:

1. A method for the detection and determination of one or more analytes in a sample of a biological material, which method comprises the steps of;

a) adsorbing a binding partner specific for the one or more analytes onto a regenerable precious metal solid phase;

b) contacting the sample of the biological material with the regenerable solid phase;

c) determining the amount of the one or more analytes bound to the regenerable solid phase;

d) determining the prescence or amount of the one or more analytes in the sample from the amount of the one or more analytes bound to the regenerable solid phase; and e) regenerating the regenerable solid phase by desorbing the binding partner specific for the one or more analytes from the regenerable solid phase;

wherein said regenerated solid phase is capable of adsorbing the same or a different binding partner onto the regenerable solid phase and repeating steps b)–e).

2. The method as claimed in claim 1, wherein a reagent is used in step e) that desorbs the binding partner without damaging the regenerable solid phase.

3. The method as claimed in claim 2, wherein the reagent comprises a reducing agent.

4. The method as claimed in claim 2, wherein the reagent comprises an oxidizing agent.

5. The method as claimed in claim 2, wherein the reagent comprises $NaBH_4$.

6. The method as claimed in claim 2, wherein the reagent comprises tetrabutylammonium hydroxide.

7. The method as claimed in claim 1 wherein the precious metal is gold.

8. The method as claimed in claim 1, wherein the regenerable solid phase is coated on a support.

9. The method as claimed in claim 8, wherein the precious metal is gold.

10. The method as claimed in claim 8, wherein support is a tube.

11. The method as claimed in claim 1, wherein the specific binding partner is an immunoglobulin.

* * * * *